US00PP13347P2

(12) United States Plant Patent
Taylor

(10) Patent No.: US PP13,347 P2
(45) Date of Patent: Dec. 10, 2002

(54) *AGARISTA POPULIFOLIA* PLANT NAMED 'TAYLOR'S TREASURE'

(75) Inventor: David William Taylor, Semmes, AL (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 09/887,012

(22) Filed: Jun. 25, 2001

(51) Int. Cl.[7] ..... A01H 5/00
(52) U.S. Cl. ..... Plt./226
(58) Field of Search ..... Plt./226

*Primary Examiner*—Kent L. Bell

(57) ABSTRACT

A new and distinct variety of *Agarista populifolia* plant which possesses a low compact growth habit, reddish-bronze undulate shaped immature foliage, and fragrant white flowers.

1 Drawing Sheet

BACKGROUND OF THE INVENTION

The present invention relates to a new and distinct cultivar of Agarista, botanically known as *Agarista populifolia*, and hereinafter referred to by the cultivar name 'Taylor's Treasure'. This new Agarista variety was discovered by David W. Taylor in the summer of 1995 as an openly pollinated seedling in a group of unnamed, unpatented *Agarista populifolia* plants at Taylor's Nursery in Semmes, Ala. The value of this new cultivar lies in its unique compact growth habit and attractive reddish-bronze undulate shaped immature foliage. 'Taylor's Treasure' has retained many of the outstanding attributes of the parent species, in particular its tolerance of insects and disease which makes it adaptable to culture in the Sunbelt states.

Asexual propagation of the new plant by cuttings has been under Mr. Taylor's direction at the same location. The new plant retains its distinctive characteristics and reproduces true to the type in successive generations. The plant cannot be reproduced true from seed.

SUMMARY OF THE INVENTION

The following are the most outstanding and distinguishing characteristics of this new cultivar when grown under normal horticultural practices in Semmes, Ala.

1. Low compact growth habit.
2. The reddish-bronze color and undulate margins of the immature foliage is unique and offers a novel and strikingly appealing contrast of new foliage to old foliage in plants of this market class.
3. Attractive bell-shaped, fragrant white flowers.
4. Numerous flowers per plant.
5. Attractive evergreen foliage.
6. Fast growth rate under normal fertilization and moisture conditions.
7. Easily propagated with semi-hardwood cuttings in late spring through the summer.
8. Tolerates full sun to shade.
9. Good specimen plant.
10. Desirable in planters.
11. Hardy to Zone 6.

DESCRIPTION OF THE DRAWINGS

This new *Agarista populifolia* variety is illustrated by the accompanying photographic prints in which:

1. The photograph at the top of the sheet is a close-up view of the typical flower, foliage, and stem color as well as flower size and form of 'Taylor's Treasure'.
2. The photograph at the bottom of the sheet shows the low compact growth habit and foliage color of a young three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Agarista based on my observations made of 2 year old plants grown in 3 gallon containers in commercial production practices, in greenhouses, and in established landscape plantings in Semmes, Ala.

DISTINCTIVE CHARACTERISTICS

| Characteristic | *Agarosta p.* 'Taylor's Treasure' | *Agarosta p.* (The species) |
|---|---|---|
| Height (Mature) | 3–5' | 8–12' |
| Width (Mature) | 2–3' | 8–10' |
| Leaf Length | 1–2¾" | 1½–4" |
| Leaf Width | ½–⅞" | ½–1½" |
| Leaf Curvature (Immature) | Undulate | Almost Flat |
| Foliage Color (Immature) | Greyed-Orange G. 171A to 172A | Greyed-Orange G. 171A to 172A |
| Foliage Color (Mature) | Green G. 137A | Green G. 137A |
| Growth Habit | Low Compact | Mounding to Arching |
| Internode Length | ⅛–½" | 3/16–¾" |
| Flower Length | 5/16–½" | ⅜–⅝" |
| Flower Diameter | 3/16–5/16" | ¼–⅜" |

Agarista 'Taylor's Treasure' is similar to the parent species *Agarista populifolia*, however, in side-by-side comparisons conducted in Semmes, Ala., 'Taylor's Treasure' produced a smaller more compact plant. The leaves of 'Taylor's Treasure' are smaller and narrower than the parent species.

Classification

Botanic: *Agarista populifolia* 'Taylor's Treasure'.
Commercial: Broadleaf evergreen.
Form: Low and compact.
Height: 3–5'.
Width: 2–3'.

Growth rate: Fast under normal fertilization and moisture conditions in Semmes, Ala. Mature height is 3–5' and width 2–3'. This varies greatly from the parent species which can grow to 12' tall. Semi-hardwood cuttings taken in late spring through the summer produce rooted cuttings in 3–4 months. Root development is vigorous and finely branched. From a rooted cutting, the new variety reaches a height of 3' and a spread of 2' in a period of four years. The growth rate is normally about 8–10" per year while maintaining a dense habit due to the abundant branch development and short internode lengths.

Foliage: Alternate, simple, evergreen, lanceolate to ovate-lanceolate, 1 to 2¾" long and ¼" to ⅞" wide. Apex is acute to acuminate; the base is rounded; the margins are serrulate and, occasionally, entire. Immature foliage is often undulate. The petioles are 1/16" to 3/16" long and puberulent. Leaf venation is pinnate. Mid-ribs are impressed on the upper surface and prominent on the underside. The veins, other than the mid-rib, are generally not visible on the underside of the leaf. The upper surface of the immature leaves are glossy, glabrous, and pronounced with a reddish-bronze coloration Greyed-Orange Group 171A to 172A. The underside is Greyed-Orange Group 174B and matte. The fully expanded immature leaves are Yellow-Green Group 144A top and Yellow-Green Group 144B bottom. The mature leaves are Green Group 137A, dull and glabrous on top and Green Group 137C and matte beneath. These mature leaf colorations are persistant throughout the winter. Mid-ribs are Yellow-Green Group 144A top and bottom. The smaller leaf venations on top of the leaf are also Yellow-Green Group 144A. Immature petioles are Yellow-Green Group 144C overlaid with Greyed-Orange Group 173A and mature to Yellow-Green Group 144B.

The immature foliage of 'Taylor's Treasure' has an undulate shape compared to the parent species whose new foliage is flat. As the foliage expands it becomes almost flat. This undulate leaf shape addes to the attractiveness of the new variety.

In 1998, the date of initial spring growth was March 5, in Semmes, Ala. After the initial spring flush, there was almost continuous growth until fall, ending October 27, also in Semmes, Ala. This growth pattern was identical to the parent species. When grown in full sun, the internode length of 'Taylor's Treasure' is ⅛" to ⅜" compared to 3/16" to ½" for the parent species. When grown in light shade, the internode length is ¼" to ½" for 'Taylor's Treasure' and ⅜" to ¾" for the parent species. As would be expected, either plant grown in the shade results in a taller, less dense plant with larger leaves.

Stems: The young shoots are Greyed-Orange Group 174A and puberulent. In about a month they change to Yellow-Green Group 144B. After one or more years the stems are generally Greyed-Brown Group 199A, glabrous, and rugose. The plant is densely branched throughout the entire shrub. The pith is lamellate and hollow at maturity.

Flowers: Perfect, fragrant, axillary, 3–9 per raceme, borne on previous year's wood, 5/16" to ½" long and 3/16" to 5/16" in diameter. Peduncle is puberulent, 5/16" to ¾" long. Yellow-Green Group 144B, and overlaid with Greyed-Red Group 178A. Pedicels are puberulent, 3/16" to ¼" long, curved near the end, Yellow-Green Group 145A, and ofter overlaid with Greyed-Red Group 178A near the base. Pedicels have 1 to 3 bracteoles (Yellow-Green Group 145A) to 1/16" long near the base. Calyx lobes are triangular, 5-parted, 1/16" long and Yellow-Green Group 145A. The corolla is gamopetalous, urceolate to cylindrical, distally 5-lobed, White Group 155C and slightly transparent. The pistil is single, 5/16" to 9/16" long, often exserted, Yellow-Green Group 145C. The ovary is Yellow-Green Group 144B. The stamens are ⅛" to 1/16" long and regularly arranged around the style. The filaments are puberulent and White Group 155C. The anthers are 1/16" long, Greyed-Orange Group 169B and the pollen is Yellow Group 4B. There is a 2 to 4 week flowering period normally beginning in early April in Semmes, Ala. The blooms last on the plant in the garden 10 to 14 days. A mature plant may have several hundred flowers. Flowers have a sweet fragrance.

Fruit: Capsule depressed, oblate, 3/16" to ¼" long, ¼" to 5/16" wide. Each capsule contains 8–12 glabrous seeds which are 1/32" to 1/16" long. The capsule matures from Yellow-Green Group 144B in the spring to Greyed-Brown Group 199A in September and October. The capsule opens in the fall to release the seeds which are Greyed-Orange Group 165C. Normal fruit set is not heavy.

Culture: Grows well in a wide range of conditions and tolerates sun to shade. Prefers a moist, well-drained soil that is rich in organic matter. Responds well to mulching and medium applications of fertilizer; prefers ph 5.0 to 6.5. Very little pruning is needed; adaptable to container and above ground planters; makes a good foundation plant or low-growing informal hedge. Ideal for coastal regions and warmer parts of the Piedmont. Cold hardiness and resistance to insects, disease, and drought are comparable to the parent species.

I claim:

1. A new and unique variety of *Agarista populifolia* plant named 'Taylor's Treasure' as herein shown and described.

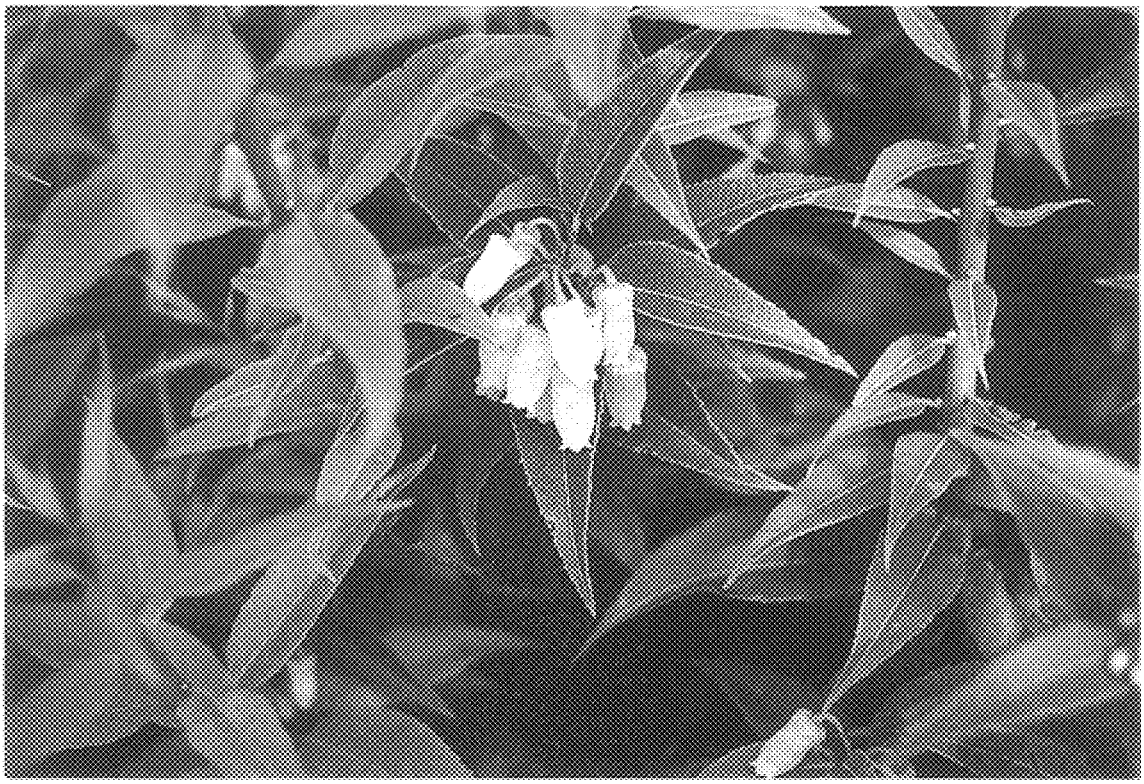
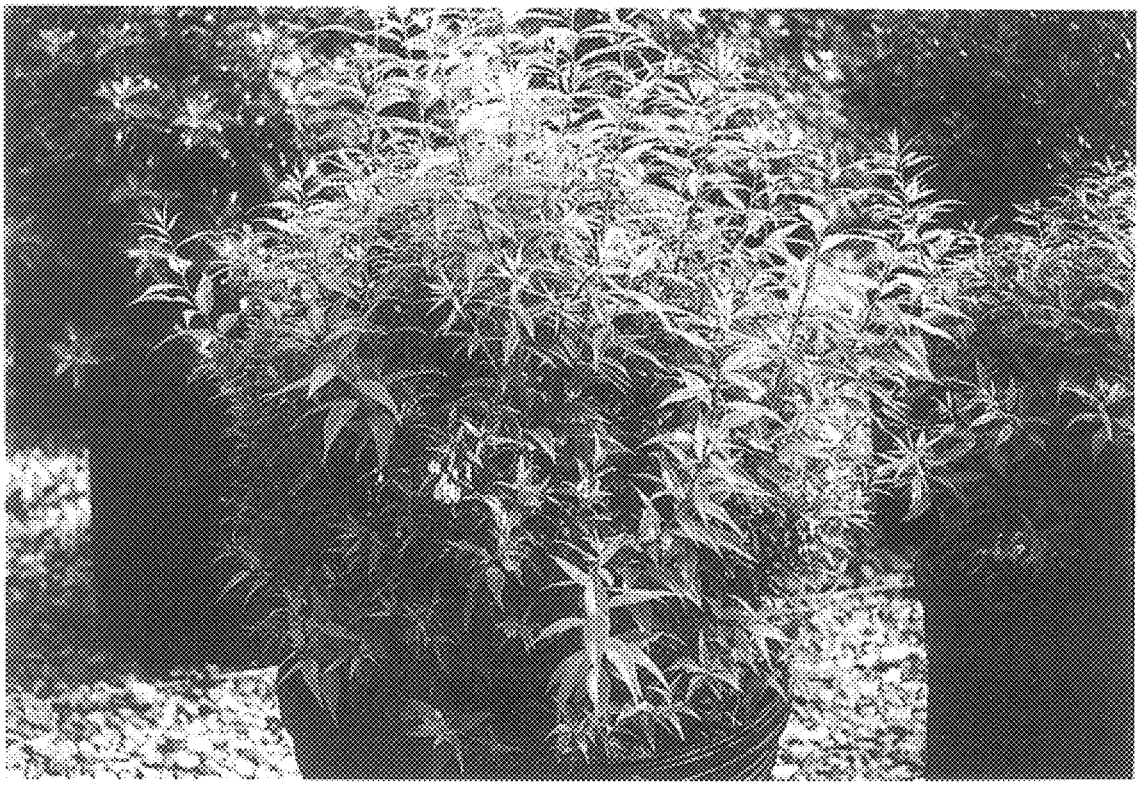

* * * * *